United States Patent
Jinwal et al.

(10) Patent No.: US 10,653,642 B2
(45) Date of Patent: *May 19, 2020

(54) COMPOSITIONS AND METHODS FOR THE TREATMENT OF TAUOPATHIES

(71) Applicant: UNIVERSITY OF SOUTH FLORIDA, Tampa, FL (US)

(72) Inventors: Umesh Kumar Jinwal, Temple Terrace, FL (US); Vetriselvan Manavalan, Brandon, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/293,535

(22) Filed: Mar. 5, 2019

(65) Prior Publication Data

US 2019/0298663 A1    Oct. 3, 2019

Related U.S. Application Data

(63) Continuation of application No. 15/905,748, filed on Feb. 26, 2018.

(60) Provisional application No. 62/463,408, filed on Feb. 24, 2017.

(51) Int. Cl.
*A61K 9/00* (2006.01)
*A61P 25/28* (2006.01)
*A61K 31/055* (2006.01)

(52) U.S. Cl.
CPC .......... *A61K 31/055* (2013.01); *A61K 9/0019* (2013.01); *A61P 25/28* (2018.01)

(58) Field of Classification Search
CPC ...... A61K 31/055; A61K 9/0019; A61P 25/28
See application file for complete search history.

(56) References Cited

U.S. PATENT DOCUMENTS

| | | |
|---|---|---|
| 4,554,101 A | 11/1985 | Hopp |
| 5,580,859 A | 12/1996 | Felgner et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Felgner et al. |
| 6,068,650 A | 5/2000 | Hofmann et al. |
| 6,096,020 A | 9/2000 | Hofmann |
| 6,120,493 A | 9/2000 | Hofmann |
| 6,181,964 B1 | 1/2001 | Hofmann et al. |
| 6,192,270 B1 | 2/2001 | Hofmann et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,302,874 B1 | 10/2001 | Zhang et al. |
| 7,664,545 B2 | 2/2010 | Westersten et al. |
| 9,150,148 B2 | 10/2015 | Baudru et al. |
| 2013/0116215 A1* | 5/2013 | Coma ............ A61K 31/165 514/108 |
| 2016/0136123 A1* | 5/2016 | Deretic .............. C12Q 1/61 424/450 |

OTHER PUBLICATIONS

Iqbal et al. Curr Alzheimer Res. Dec. 2010; 7(8): 656-664.*
Abisambra et al., "Tau Accumulation Activates the Unfolded Protein Response by Impairing Endoplasmic Reticulum-Associated Degradation," J. Neurosci., 2013, 33, 9498-9507.
Barghorn et al., "Tau Paired Helical Filaments from Alzheimer's Disease Brain and Assembled in Vitro Are Based on β-Structure in the Core Domain," Biochem, 2004, 43, 1694-1703.
Bryan et al., "Transgenic Mouse Models of Alzheimer's Disease: Behavioral Testing and Considerations," Methods of Behavior Analysis in Neuroscience, 2009, Chapter 1.
C.T.F.A. Cosmetic Ingredient Handbook, 1992, pp. 587-592.
Cohen et al., "TDP-43 functions and pathogenic mechanisms implicated in TDP-43 proteinopathies," Trends Mol Med, 2011, 17, 659-67.
Dehmelt et al., "The MAP2/Tau family of microtubule-associated proteins," S. Genome Biol., 2005, 6, 204.
Donnelly et al., "DNA vaccines," Ann. Rev. Immunol., 1997, 15:617-648.
Gustke et al., "Domains of τ protein and interactions with microtubules," Biochem, 1994, 33, 9511-9522.
Heagerty et al., "Time-dependent ROC curves for censored survival data and a diagnostic marker," Biometrics, 2000, 56(2):337-344.
Jeganathan et al., "The natively unfolded character of tau and its aggregation to Alzheimer-like paired helical filaments," Biochem, 2008, 47, 10526-10539.
Jinwal et al., "Chemical Manipulation of Hsp70 ATPase Activity Regulates Tau Stability," J. Neurosci., 2009, 29, 12079-12088.
Kyte et al., "A Simple Method for Displaying the Hydropathic Character of a Protein," J. Mol. Biol. 1982, 157, 105-132.
Manavalan et al., "Hexachlorophene reduces Tau aggregation and potential therapeutic agent for treatment of Alzheimer's disease," Poster presented at USF Health Research Day, Feb. 24, 2017.
McCutcheon's vol. 1, Emulsifiers & Detergents, 1994, North American Edition, pp. 236-239.

(Continued)

*Primary Examiner* — Shirley V Gembeh

(74) *Attorney, Agent, or Firm* — Meunier Carlin & Curfman LLC

(57) ABSTRACT

Disclosed herein are compositions and methods for treating tauopathies such as Alzheimer's disease (AD). Also provided herein are methods of reducing or disrupting tau aggregation in a subject, and methods of reducing tau protein in a subject. The methods may include administering to the subject a therapeutic amount of hexachlorophene, or a pharmaceutically acceptable salt thereof. Further provided herein are pharmaceutical compositions comprising hexachlorophene, or a pharmaceutically acceptable salt thereof, for the treatment of a tauopathy in a subject.

22 Claims, 14 Drawing Sheets

(56) References Cited

OTHER PUBLICATIONS

Remington's Pharmaceutical Sciences, 15th Ed. 1975, pp. 335-337.
Sui et al., "In Vitro Aggregation Assays Using Hyperphosphorylated Tau Protein," Journal of Visualized Experiments, 2015, 95:51537.
Von Bergen et al., "Tau aggregation is driven by a transition from random coil to beta sheet structure," Biochim. Biophys. Acta, 2005, 1739, 158-166.

\* cited by examiner

COMPOSITIONS AND METHODS FOR THE TREATMENT OF TAUOPATHIES

CROSS-REFERENCE TO RELATED APPLICATION(S)

This application is a continuation of U.S. patent application Ser. No. 15/905,748, filed on Feb. 26, 2018, which claims priority to U.S. Provisional Patent Application No. 62/463,408, filed on Feb. 24, 2017, each of which is incorporated herein by reference in its entirety.

FIELD

This disclosure relates to methods and compositions for the treatment of tauopathies such as Alzheimer's disease (AD).

INTRODUCTION

An emerging number of tauopathies continue to impact neuronal health and show causal impact on cognitive impairment and neuronal loss. The microtubule-associated protein tau can form neurotoxic aggregates that promote cognitive deficits in tauopathies. AD is the most common tauopathy. AD is a rapidly progressive neurodegenerative disease that affects over 5 million people in the United States alone. The molecular mechanism of AD pathogenesis is not completely understood, and there only exist very few pharmacological means of intervention for the disease.

SUMMARY

In an aspect, the disclosure relates to methods of treating a tauopathy in a subject. The method may include administering to the subject a therapeutic amount of hexachlorophene, or a pharmaceutically acceptable salt thereof.

In a further aspect, the disclosure relates to methods of reducing or disrupting tau aggregation in a subject. The method may include administering to the subject a therapeutic amount of hexachlorophene, or a pharmaceutically acceptable salt thereof.

Another aspect of the disclosure provides methods of reducing tau protein in a subject. The method may include administering to the subject a therapeutic amount of hexachlorophene, or a pharmaceutically acceptable salt thereof.

In some embodiments, the level of phosphorylated tau protein is reduced. In some embodiments, the level of total tau protein is reduced. In some embodiments, the level is reduced a least 10%. In some embodiments, the level is reduced at least 50%. In some embodiments, the level is reduced at least 80%. In some embodiments, tau aggregation is reduced. In some embodiments, tau aggregation is reduced a least 10%. In some embodiments, tau aggregation is reduced at least 50%. In some embodiments, tau aggregation is reduced at least 80%.

In some embodiments, the tauopathy is selected from neurodegenerative disease, Alzheimer's disease (AD), Parkinson's disease, Huntington's disease, neuronal loss, cognitive defect, primary age-related tauopathy (PART)/Neurofibrillary tangle-predominant senile dementia, chronic traumatic encephalopathy including dementia pugilistica, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis. In some embodiments, the tauopathy comprises Alzheimer's disease (AD).

In some embodiments, the hexachlorophene or salt is present in a therapeutically effective amount in a pharmaceutical composition. In some embodiments, the hexachlorophene or salt is administered to the subject intravenously, intraarterially, or intraperitoneally. In some embodiments, the hexachlorophene or salt is delivered to the brain of the subject. In some embodiments, the hexachlorophene or salt is administered by gavage.

Another aspect of the disclosure provides a pharmaceutical composition comprising hexachlorophene, or a pharmaceutically acceptable salt thereof, for the treatment of a tauopathy in a subject. In some embodiments, the tauopathy comprises Alzheimer's disease (AD).

The disclosure provides for other aspects and embodiments that will be apparent in light of the following detailed description and accompanying figures.

DETAILED DESCRIPTION

Figure 1A:
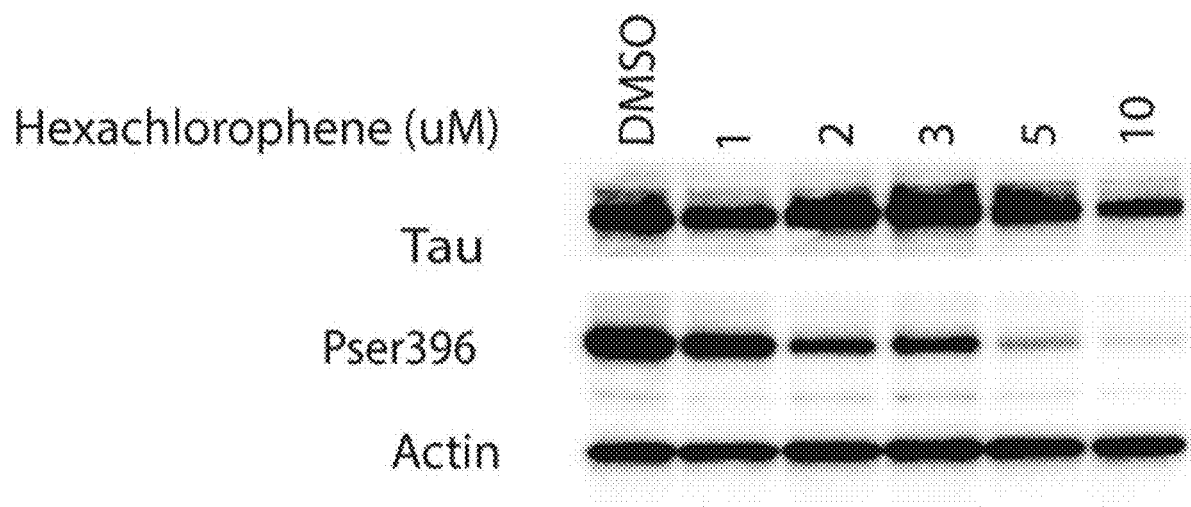
FIG. 1A is a Western blot of M17 neuroblastoma cell lysate samples probed with antibodies for total tau, phosphorylated tau, and actin (as a control), after treatment with various amounts of hexachlorophene.

Described herein is hexachlorophene, compositions comprising hexachlorophene, and the use in treating tauopathies. It was discovered that hexachlorophene reduces the total level of tau protein in a cell, the level of phosphorylated tau protein, tau aggregation, or a combination thereof. Hexachlorophene may be used in therapeutics to reduce toxic tau oligomers and treat or slow or prevent tauopathies and the progression thereof.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "administration" or "administering," as used herein, refers to providing, contacting, and/or delivery of an agent or compound by any appropriate route to achieve the desired effect. These agents or compounds may be administered to a subject in numerous ways including, but not limited to, orally, ocularly, nasally, intravenously, topically, as aerosols, suppository, etc. and may be used in combination.

The term "agonist" refers to a biologically active ligand that binds to its complementary biologically active receptor and activates the receptor either to cause a biological response in the receptor or to enhance a biological activity of the receptor. An agonist may trigger (e.g., initiate or promote), partially or fully enhance, stimulate, or activate one or more biological activities. An agonist may mimic the action of a naturally occurring substance.

"Antagonist" or "inhibitor" refers to an agent that inhibits the effect of an agonist. An antagonist may be a compound that inhibits or reduces an activity of a polypeptide. An antagonist may indirectly or directly bind a polypeptide and inhibit the activity of the polypeptide, including binding activity or catalytic activity. For example, an antagonist may prevent expression of a polypeptide, or inhibit the ability of a polypeptide to mediate the binding of the polypeptide to a ligand. An "allosteric antagonist" refers to a compound that binds to a polypeptide at a secondary site, distinct from the primary ligand binding site, and inhibits or reduces an activity of the polypeptide.

The terms "inhibit" or "inhibiting" mean that an activity is decreased or prevented in the presence of an inhibitor as opposed to in the absence of the inhibitor. The term "inhibition" refers to the reduction or down regulation of a process or the elimination of a stimulus for a process, which results in the absence or minimization of the expression or activity of a biomolecule or polypeptide. Inhibition may be direct or indirect. Inhibition may be specific, that is, the inhibitor inhibits a biomolecule or polypeptide and not others.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject, or a sample therefrom, whose disease state is known. The subject, or sample therefrom, may be healthy, diseased, diseased prior to treatment, diseased during treatment, or diseased after treatment, or a combination thereof. The term "normal subject" as used herein means a healthy subject, i.e. a subject having no clinical signs or symptoms of disease. The normal subject may be clinically evaluated for otherwise undetected signs or symptoms of disease, which evaluation may include routine physical examination and/or laboratory testing. In some embodiments, the control is a healthy control. In some embodiments, the control comprises neurodegenerative disease.

"Neurodegenerative Diseases" are disorders characterized by, resulting from, or resulting in the progressive loss of structure or function of neurons, including death of neurons. Neurodegeneration can be found in many different levels of neuronal circuitry ranging from molecular to systemic. Some neurodegenerative diseases occur as a result of neurodegenerative processes. Some neurodegenerative diseases are caused by genetic mutations. Some neurodegenerative diseases are classified as proteopathies, such as tauopathies, because they are associated with the aggregation of misfolded proteins. Neurodegenerative diseases include, for example, Alzheimer's Disease (AD), amyotrophic lateral sclerosis (ALS), Parkinson's Disease (PD), Huntington's Disease, prion disease, motor neuron disease, spinocerebellar ataxia, spinal muscular atrophy, neuronal loss, cognitive defect, primary age-related tauopathy (PART)/Neurofibrillary tangle-predominant senile dementia, chronic traumatic encephalopathy including dementia pugilistica, dementia with Lewy bodies, neuroaxonal dystrophies, and multiple system atrophy, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be, for example, 2 to 20, 2 to 15, or 2 to 10 amino acids in length. In some embodiments, a motif includes 3, 4, 5, 6, or 7 sequential amino acids. A domain may be comprised of a series of the same type of motif.

"Sample" or "test sample" as used herein can mean any sample in which the presence and/or level of a target, agent, or activity is to be detected or determined. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

The term "specificity" as used herein refers to the number of true negatives divided by the number of true negatives plus the number of false positives, where specificity ("spec") may be within the range of 0<spec<1. Ideally, the methods described herein have the number of false positives equaling zero or close to equaling zero, so that no subject is wrongly identified as having a disease when they do not in fact have disease. Hence, a method that has both sensitivity and specificity equaling one, or 100%, is preferred.

By "specifically binds," it is generally meant that an agent or polypeptide binds to a target when it binds to that target more readily than it would bind to a random, unrelated target.

"Subject" as used herein can mean a mammal that wants or is in need of the herein described therapies and compositions. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant. In some embodiments, the subject is human. In some embodiments, the subject has a specific genetic marker.

"Substantially identical" can mean that a first and second amino acid or polynucleotide sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids or nucleotides.

A "therapeutically effective amount," or "effective dosage," or "effective amount" as used interchangeably herein unless otherwise defined, means a dosage of an agent, compound, or drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in a subject. A therapeutically effective amount may be administered in one or more administrations (e.g., the composition may be given as a preventative treatment or therapeutically at any stage of disease progression, before or after symptoms, and the like), applications, or dosages, and is not intended to be limited to a particular formulation, combination, or administration route. It is within the scope of the present disclosure that the agent, compound, or drug may be administered at various times during the course of treatment of the subject. The times of administration and dosages used will depend on several factors, such as the goal of treatment (e.g., treating v. preventing), condition of the subject, etc. and can be readily determined by one skilled in the art. A therapeutically effective amount is also one in which any toxic or detrimental effects of substance are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The terms "treat," "treated," or "treating" as used herein refers to a therapeutic wherein the object is to slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment. The terms "treat," "treated," or "treating" may include preventing, suppressing, repressing, ameliorating, or completely eliminating the disease. Preventing the disease may involve administering a composition of the present invention to a subject prior to onset of the disease. Suppressing the disease may involve administering a composition of the present invention to a subject after induction of the disease but before its clinical appearance. Repressing or ameliorating the disease may involve administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide, to bind a ligand, or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof. In some embodiments, variants include homologues. Homologues may be polynucleotides or polypeptides or genes inherited in two species by a common ancestor.

2. NEURODEGENERATIVE DISEASES

The compositions and methods as detailed herein may be used to treat tauopathies. Tauopathies are a type of proteinopathy, which is a type of neurodegenerative disease.

Proteinopathies are diseases or disorders in which a protein becomes structurally abnormal. For example, the protein may fail to properly fold into its normal configuration, e.g., become misfolded. In some embodiments, the proteins form aggregates. Protein misfolding may include changes to the secondary and/or tertiary structure of a protein. For example, a protein may become structurally abnormal by increasing the beta-sheet secondary structure of the protein. The abnormal structure of the protein may disrupt its function, such as gaining a new function or losing normal function. The structurally abnormal protein may thereby disrupt the function of cells, tissues, and/or organs. Proteinopathies may also be referred to as proteopathies, protein confirmation disorders, or protein misfolding diseases. Proteinopathies may be associated with protein aggregation and ultimately cell demise. Proteinopathies include, for example, tauopathies, synucleopathies, and disorders characterized by the aggregation of amyloid-beta peptides. Proteinopathies may also include prion disease and amyloidosis.

a. Tau

In some embodiments, the compositions and methods as detailed herein modulate the tau protein, to treat tauophathies. Tau is a protein that associates with and stabilizes microtubules. Tau may also be referred to as microtubule associated protein tau (MAPT). Tau proteins may also interact with tubulin to stabilize microtubules and promote tubulin assembly into microtubules. There are six isoforms of Tau. Tau proteins are abundant in neurons of the central nervous system and are also expressed at very low levels in central nervous system (CNS) astrocytes and oligodendrocytes. Tau protein may play a role in stabilizing microtubule networks in neurons.

Tau protein may be phosphorylated by a host of kinases. Phosphorylation of tau is developmentally regulated. Excessive phosphorylation (hyperphosphorylation) or abnormal phosphorylation of tau may result in disruption of microtubule organization, accumulation, and/or aggregation of tau proteins. In some embodiments, tau aggregates do not function properly. For example, tau aggregates may not stabilize microtubules properly.

Tau aggregates include, for example, PHF-tau (paired helical filament), NFTs (neurofibrillary tangles), and gliofibrillary tangles. Tau aggregates may also be described as monomeric, or high molecular weight multimers. Tau aggregates may be insoluble. Tau aggregates may be present in the brain. Tau proteins may be deposited in the form of inclusion bodies within swollen neurons. Aggregation of tau into oligomeric species may lead to various pathologies called tauopathies and may be a major contributor to disease progression.

The compositions and methods as detailed herein may inhibit or reduce the level of tau protein, inhibit or reduce the level of total tau protein in a cell, inhibit or reduce the level of phosphorylated tau protein, inhibit or reduce or disrupt the aggregation of tau protein, or a combination thereof. The level may be reduced by at least about 10%, at least about 20%, at least about 30%, at least about 40%, at least about 50%, at least about 60%, at least about 70%, at least about 80%, at least about 90%, at least about 95%, or at least about 98%. Tau aggregation may be reduced by at least about 10%, at least about 20%, at least about 30%, at least about 40%, at least about 50%, at least about 60%, at least about 70%, at least about 80%, at least about 90%, at least about 95%, or at least about 98%.

b. Tauopathies

Tauopathies are a class of neurodegenerative diseases associated with the pathological aggregation of tau protein. Tauopathies include, for example, Alzheimer's disease (AD), Parkinson's disease, Huntington's disease, neuronal loss, cognitive defect, primary age-related tauopathy (PART)/Neurofibrillary tangle-predominant senile dementia, chronic traumatic encephalopathy including dementia pugilistica, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis. In some embodiments, the taupoathy comprises Alzheimer's disease (AD).

The compositions and methods as detailed herein may inhibit or reduce the level of tau protein, inhibit or reduce the level of total tau protein in a cell, inhibit or reduce the level of phosphorylated tau protein, inhibit or reduce or disrupt the aggregation of tau protein, or a combination thereof, to treat a tauopathy.

3. HEXACHLOROPHENE

Provided herein are compositions and methods relating to the compound hexachlorophene. The structure of hexachlorophene is shown below:

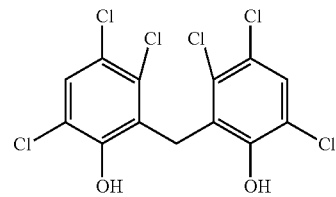 [SMILES: Oc1c(Cl)cc(Cl)c(Cl)c1Cc1c(O)c(Cl)cc(Cl)c1Cl]

Hexachlorophene, upon administration to a subject, may elicit a variety of effects. In some embodiments, hexachlorophene inhibits or reduces the level of tau protein. In some embodiments, hexachlorophene inhibits or reduces the level of total tau protein in a cell. In some embodiments, hexachlorophene inhibits or reduces the level of phosphorylated tau protein. In some embodiments, hexachlorophene inhibits or reduces tau accumulation. In some embodiments, hexachlorophene inhibits or reduces tau aggregation. By affecting tau protein, hexachlorophene may slow, prevent, or treat a tauopathy or neurodegenerative disease progression, or a combination thereof.

The activity of hexachlorophene may be examined by, for example, measuring the amount of tau protein, measuring the aggregation of tau protein, or measuring the amount of neurons in a cell line or post-mortem brain samples, or a combination thereof. Suitable methods are known in the art and may include, for example, microscopy, immunohistochemistry, thioflavin S assay, and Western blot analysis. The activity of hexachlorophene may be examined by administering hexachlorophene to mice before, concomitantly, or after assessing the mice for cognitive function in assays such as radial arm water maze (RAWM; a hippocampal-dependent spatial learning task that does not rely on locomotor ability or swimming speed); rotating cylinder (rotarod; for testing motor balance and coordination); fear conditioning and passive-avoidance learning assays for contextual memory; and Y-maze, T-maze, object recognition, and open field assays for working memory/novelty/activity (Bryan, K. J., et al. Transgenic Mouse Models of Alzheimer's Disease: Behavioral Testing and Considerations. In: Buccafusco J J, editor. Methods of Behavior Analysis in Neuroscience. 2nd edition. Boca Raton (Fla.): CRC Press/Taylor & Francis, 2009. Chapter 1).

Hexachlorophene is commercially available. For example, hexachlorophene is commercially available from Sigma-Aldrich (St. Louis, Mo.; catalog no. 45526). Alternatively, hexachlorophene may be synthetically made by methods known to one of skill in the art. The compound structure may be confirmed by methods known to one of skill in the art, such as, for example, mass spectrometry and NMR.

The present disclosure also includes an isotopically-labeled compound of hexachlorophene, which is identical to the compound shown above, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e. $^2H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in the compound are $^{11}C$, $^{13}N$, $^{15}O$, and $^{18}F$. Isotopically-labeled compounds can generally be prepared by conventional techniques known to those skilled in the art using appropriate isotopically-labeled reagent in place of non-isotopically-labeled reagent.

a. Pharmaceutically Acceptable Salts

The disclosed hexachlorophene compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds may also be quaternized with alkyl chlorides, bromides and iodides such as methyl, ethyl, propyl, isopropyl, butyl, lauryl, myristyl, stearyl, and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. Pharmaceutical Compositions

The hexachlorophene compounds as detailed herein may be formulated into pharmaceutical compositions in accordance with standard techniques well known to those skilled in the pharmaceutical art. The composition may comprise the compound and a pharmaceutically acceptable carrier. The term "pharmaceutically acceptable carrier," as used herein, means a non-toxic, inert solid, semi-solid or liquid filler, diluent, encapsulating material or formulation auxiliary of any type.

The route by which the disclosed compounds are administered and the form of the composition will dictate the type of carrier to be used. The pharmaceutical composition may be in a variety of forms, suitable, for example, for systemic administration (e.g., oral, rectal, sublingual, buccal, implants, intranasal, intravaginal, transdermal, intravenous, intraarterial, intratumoral, intraperitoneal, or parenteral) or topical administration (e.g., dermal, pulmonary, nasal, aural, ocular, liposome delivery systems, or iontophoresis). In some embodiments, the pharmaceutical composition is for administration to a subject's central nervous system. Techniques and formulations may generally be found in "Remington's Pharmaceutical Sciences," (Meade Publishing Co., Easton, Pa.). Pharmaceutical compositions must typically be sterile and stable under the conditions of manufacture and storage. All carriers are optional in the compositions.

Pharmaceutically acceptable carriers include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof.

Suitable diluents include, for example, sugars such as glucose, lactose, dextrose, and sucrose; diols such as propylene glycol; calcium carbonate; sodium carbonate; sugar alcohols, such as glycerin; mannitol; sorbitol; cellulose; starch; and gelatin. The amount of diluent(s) in a systemic or topical composition may typically be about 50 to about 90%.

Suitable lubricants include, for example, silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of theobroma. The amount of lubricant(s) in a systemic or topical composition may typically be about 5 to about 10%.

Suitable binders include, for example, polyvinyl pyrrolidone; magnesium aluminum silicate; starches such as corn starch and potato starch; gelatin; tragacanth; sucrose; and cellulose and its derivatives, such as sodium carboxymethylcellulose, ethyl cellulose, methylcellulose, microcrystalline cellulose, and hydroxypropyl methylcellulose. The amount of binder(s) in a systemic composition may typically be about 5 to about 50%.

Suitable disintegrants include, for example, agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition may typically be about 0.1 to about 10%.

Suitable colorants include, for example, a colorant such as an FD&C dye. When used, the amount of colorant in a systemic or topical composition may typically be about 0.005 to about 0.1%.

Suitable flavors include, for example, menthol, peppermint, and fruit flavors. The amount of flavor(s), when used, in a systemic or topical composition may typically be about 0.1 to about 1.0%.

Suitable sweeteners include, for example, aspartame and saccharin, or a combination thereof. The amount of sweetener(s) in a systemic or topical composition may typically be about 0.001 to about 1%.

Suitable antioxidants include, for example, butylated hydroxyanisole ("BHA"), butylated hydroxytoluene ("BHT"), and vitamin E. The amount of antioxidant(s) in a systemic or topical composition may typically be about 0.1 to about 5%.

Suitable preservatives include, for example, benzalkonium chloride, methyl paraben, and sodium benzoate. The amount of preservative(s) in a systemic or topical composition may typically be about 0.01 to about 5%.

Suitable glidants include, for example, silicon dioxide. The amount of glidant(s) in a systemic or topical composition may typically be about 1 to about 5%.

Suitable solvents include, for example, water, isotonic saline, ethyl oleate, glycerine, castor oils, hydroxylated castor oils, alcohols such as ethanol or isopropanol, methylene chloride, ethylene glycol monoethyl ether, diethylene glycol monobutyl ether, diethylene glycol monoethyl ether, dimethylsulfoxide, dimethyl formamide, tetrahydrofuran, and phosphate buffer solutions, and combinations thereof. The amount of solvent(s) in a systemic or topical composition is typically from about 0 to about 100%, or 0% to about 95%.

Suitable suspending agents include, for example, AVICEL RC-591 (from FMC Corporation of Philadelphia, Pa.) and sodium alginate. The amount of suspending agent(s) in a systemic or topical composition may typically be about 1 to about 8%.

Suitable surfactants include, for example, lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may typically be about 0.1% to about 5%.

Suitable emollients include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition may typically be about 5% to about 95%.

Suitable propellants include, for example, propane, butane, isobutane, dimethyl ether, carbon dioxide, nitrous oxide, and combinations thereof. The amount of propellant in a topical composition may be about 0% to about 95%.

Suitable humectants include, for example, glycerin, sorbitol, sodium 2-pyrrolidone-5-carboxylate, soluble collagen, dibutyl phthalate, gelatin, and combinations thereof. The amount of humectant in a topical composition may be about 0% to about 95%.

Suitable powders include, for example, beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition may typically be 0% to 95%.

Suitable pH adjusting additives include, for example, HCl or NaOH in amounts sufficient to adjust the pH of a topical pharmaceutical composition.

In some embodiments, the pharmaceutically acceptable carrier is a sugar such as lactose, glucose, and sucrose. In some embodiments, the pharmaceutically acceptable carrier is a starch such as, for example, corn starch and potato starch. In some embodiments, the pharmaceutically acceptable carrier is cellulose and its derivatives such as, but not limited to, sodium carboxymethyl cellulose, ethyl cellulose and cellulose acetate. In some embodiments, the pharmaceutically acceptable carrier is powdered tragacanth, malt, gelatin, or talc. In some embodiments, the pharmaceutically acceptable carrier is an excipient such as, but not limited to, cocoa butter and suppository waxes. In some embodiments, the pharmaceutically acceptable carrier is oil such as, but not limited to, peanut oil, cottonseed oil, safflower oil, sesame oil, olive oil, corn oil and soybean oil. In some embodiments, the pharmaceutically acceptable carrier is a glycol, such as propylene glycol. In some embodiments, the pharmaceutically acceptable carrier is an ester such as, but not limited to, ethyl oleate and ethyl laurate. In some embodiments, the pharmaceutically acceptable carrier is an agar. In some embodiments, the pharmaceutically acceptable carrier is a buffering agent such as, but not limited to, magnesium hydroxide and aluminum hydroxide. In some embodiments, the pharmaceutically acceptable carrier is alginic acid, pyrogen-free water, isotonic saline, Ringer's solution, ethyl alcohol, or a phosphate buffer solution. In some embodiments, the pharmaceutically acceptable carrier is a non-toxic compatible lubricant such as, but not limited to, sodium lauryl sulfate and magnesium stearate.

Compositions for oral administration can have various dosage forms. For example, solid forms include tablets, capsules, granules, and bulk powders. Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Capsules (including implants, time release, and sustained release formulations) typically include a compound, and a carrier including one or more diluents disclosed above in a capsule comprising gelatin. Granules typically comprise a compound, and preferably glidants such as silicon dioxide to improve flow characteristics. Implants can be of the biodegradable or the non-biodegradable type.

Compositions for oral administration can have solid forms. Solid oral compositions may be coated by conventional methods, typically with pH or time-dependent coatings, such that a compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes, and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Compositions for topical administration can be applied locally to the skin and may be in any form including solids, solutions, oils, creams, ointments, gels, lotions, shampoos, leave-on and rinse-out hair conditioners, milks, cleansers, moisturizers, sprays, skin patches, and the like. The carrier of the topical composition preferably aids penetration of the compound into the skin. In the topical compositions, the carrier includes a topical carrier. Suitable topical carriers can include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications may include propylene glycol, dimethyl isosorbide, and water, and even more particularly, phosphate buffered saline, isotonic water, deionized water, monofunctional alcohols, and symmetrical alcohols. The carrier of a topical composition may further include one or more ingredients selected from emollients, propellants, solvents, humectants, thickeners, powders, fragrances, pigments, and preservatives, all of which are optional.

Although the amounts of components in the compositions may vary depending on the type of composition prepared, in general, systemic compositions may include 0.01% to 50% of a compound and 50% to 99.99% of one or more carriers. Compositions for parenteral administration may typically include 0.1% to 10% of a compound and 90% to 99.9% of one or more carriers. Oral dosage forms may include, for example, at least about 5%, or about 25% to about 50% of a compound. The oral dosage compositions may include about 50% to about 95% of carriers, or from about 50% to about 75% of carriers. The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

c. Administration

The hexachlorophene compounds as detailed herein, or a pharmaceutically acceptable salt thereof, or the pharmaceutical compositions comprising the same, may be administered to a subject. A composition may comprise the hexachlorophene compound or salt thereof. The hexachlorophene or salt thereof as detailed above can be formulated into a composition and administered in dosages and by techniques well known to those skilled in the medical arts taking into consideration such factors as the age, sex, weight, and condition of the particular subject, and the route of administration.

Hexachlorophene or salt thereof can be administered prophylactically or therapeutically. In prophylactic administration, hexachlorophene can be administered in an amount sufficient to induce a response. In therapeutic applications, hexachlorophene can be administered to a subject in need thereof in an amount sufficient to elicit a therapeutic effect. Hexachlorophene may be administered in a therapeutically effective amount.

For example, a therapeutically effective amount of hexachlorophene or a pharmaceutically acceptable salt thereof, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

Hexachlorophene or salt thereof can be administered by methods well known in the art as described in Donnelly et al. (Ann. Rev. Immunol. 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. Hexachlorophene or salt thereof can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

Hexachlorophene or salt thereof can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, hexachlorophene or salt thereof is administered intravenously, intraarterially, or intraperitoneally to the subject. In some embodiments, hexachlorophene is administered by gavage. In some embodiments, hexachlorophene or salt thereof is administered via cannula and osmotic pump implantation. In some embodiments, hexachlorophene or salt thereof is delivered to the brain. Brain regions include, for example, hippocampus, cortex, striatum, and corpus callosum.

Hexachlorophene or salt thereof can be a liquid preparation such as a suspension, syrup, or elixir. Hexachlorophene or salt thereof can be incorporated into liposomes, microspheres, or other polymer matrices (such as by a method described in Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

Hexachlorophene or salt thereof may be used as a vaccine. The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241, 701; 6,233,482; 6,216,034; 6,208,893; 6,192,270; 6,181, 964; 6,150,148; 6,120,493; 6,096,020; 6,068,650; and 5,702,359, the contents of which are incorporated herein by reference in their entirety. The electroporation can be carried out via a minimally invasive device.

In some embodiments, hexachlorophene or salt thereof is administered in a controlled release formulation. Hexachlorophene or salt thereof may be released into the circulation, for example. In some embodiments, hexachlorophene or salt thereof may be released over a period of at least about 1 day, at least about 2 days, at least about 3 days, at least about 4 days, at least about 5 days, at least about 6 days, at least about 7 days, at least about 1 week, at least about 1.5 weeks, at least about 2 weeks, at least about 2.5 weeks, at least about 3.5 weeks, at least about 4 weeks, or at least about 1 month.

4. METHODS a. Methods of Treating a Tauopathy in a Subject

Provided herein are methods of treating a tauopathy in a subject. The methods may include administering to the subject a therapeutic amount of hexachlorophene, or a pharmaceutically acceptable salt thereof, as detailed herein.

b. Methods of Reducing or Tau Aggregation in a Subject

Provided herein are methods of reducing or tau aggregation in a subject. The methods may include administering to the subject a therapeutic amount of hexachlorophene, or a pharmaceutically acceptable salt thereof, as detailed herein.

c. Methods of Reducing Tau Protein in a Subject

Provided herein are methods of reducing tau protein in a subject. The methods may include administering to the subject a therapeutic amount of hexachlorophene, or a pharmaceutically acceptable salt thereof, as detailed herein.

5. EXAMPLES

Example 1

Hexachlorophene Reduces Tau in Cellular Models

It was examined whether hexachlorophene can regulate levels of tau in cellular models. Three different cells lines were treated with hexachlorophene at various different doses. M17 neuroblastoma cells were treated with 1 µM, 2 µM, 3 µM, 5 µM, and 10 µM hexachlorophene. HeLa C3 cells were treated with 0.5 µM, 1 µM, 2 µM, 3 µM, and 5 µM hexachlorophene. iHEK280 cells (an inducible tau model) were treated with 0.5 µM, 1 µM, 1.5 µM, 2 µM, and 2.5 µM hexachlorophene. Cell lysates were analyzed by Western blotting for total tau, phosphorylated tau, and actin (as a control). We also analyzed the effect of hexachlorophene on various pathological forms of tau such as the phosphoserine 396 tau form that localizes to the soluble fraction. Hexachlorophene was purchased from Sigma-Aldrich (St. Louis, Mo.). BE(2) M17 neuroblastoma cells were purchased from ATCC (Manassas, Va.). HeLa C3 cells were generated according to Jinwal et al. (J. Neurosci. 2009, 29, 12079-12088). iHEK cells were generated according to Abisambra et al. (J. Neurosci. 2013, 33, 9498-9507). Neuro-2a (N2a) mouse neuroblastoma cells overexpressing human tau-GFP were generated in house.

Figure 1B:
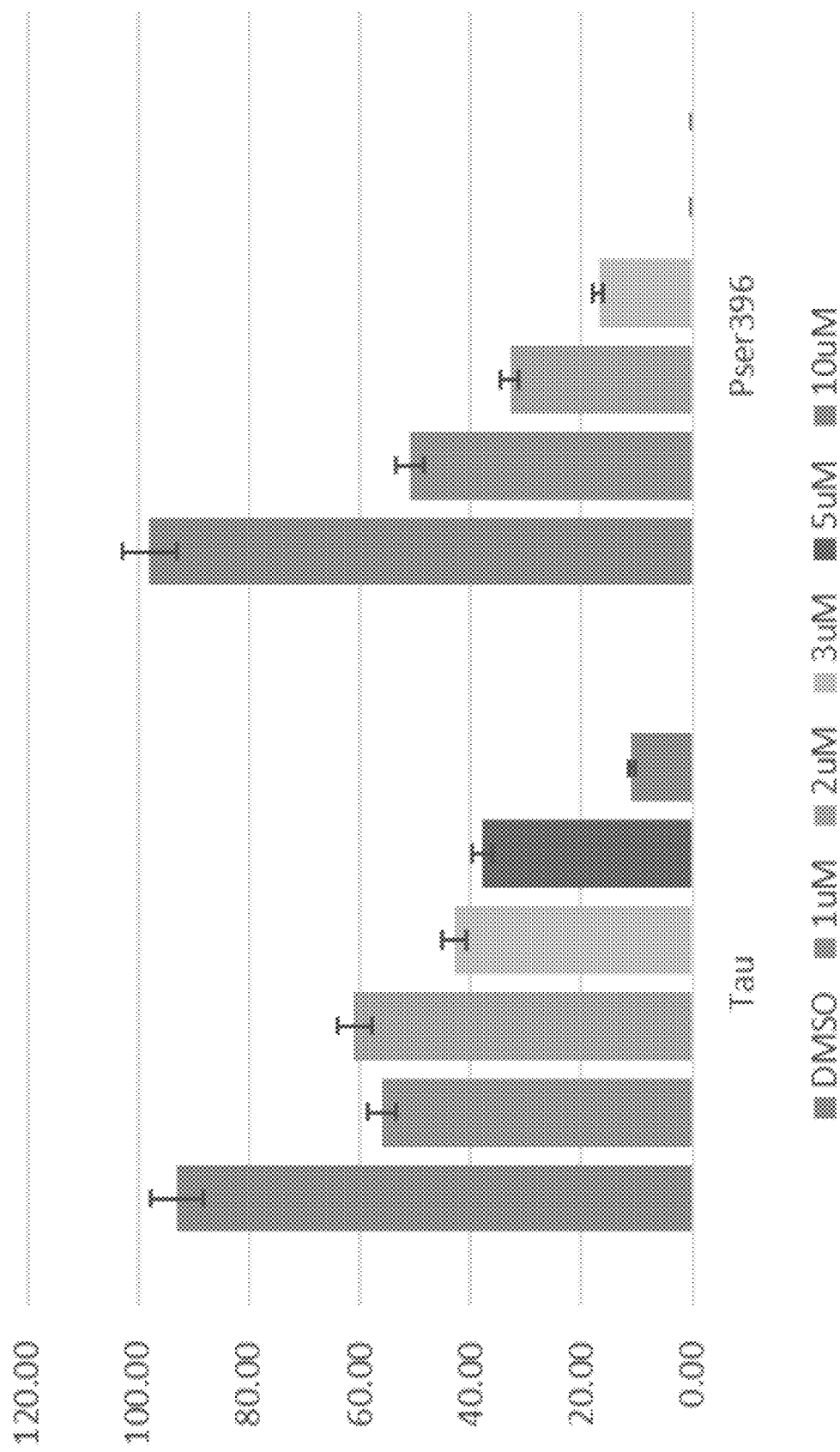
FIG. 1B is a graph showing the change in the level of total tau or phosphorylated tau after 24 hours of treatment with various amounts of hexachlorophene.

As shown in FIG. 1A and FIG. 1B, hexachlorophene decreased levels of endogenous tau in M17 neuroblastoma cells. 10 µM hexachlorophene completely cleared phosphorylated (Pser396) tau proteins.

Figure 2A:
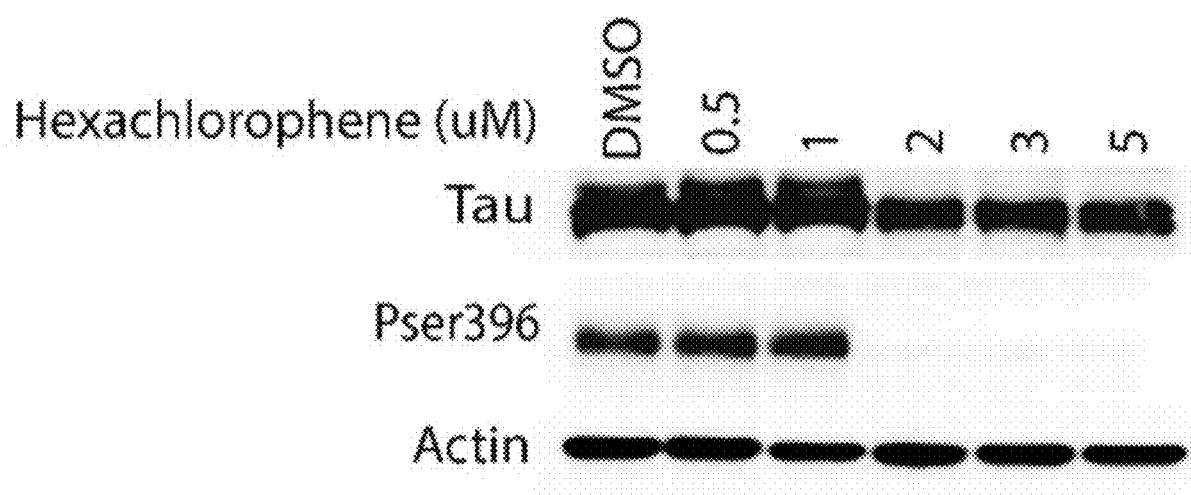
FIG. 2A is a Western blot of cell lysates from HeLa C3 cells with over-expressed tau probed with antibodies for total tau, phosphorylated tau, and actin (as a control), after treatment with various amounts of hexachlorophene.
Figure 2B:
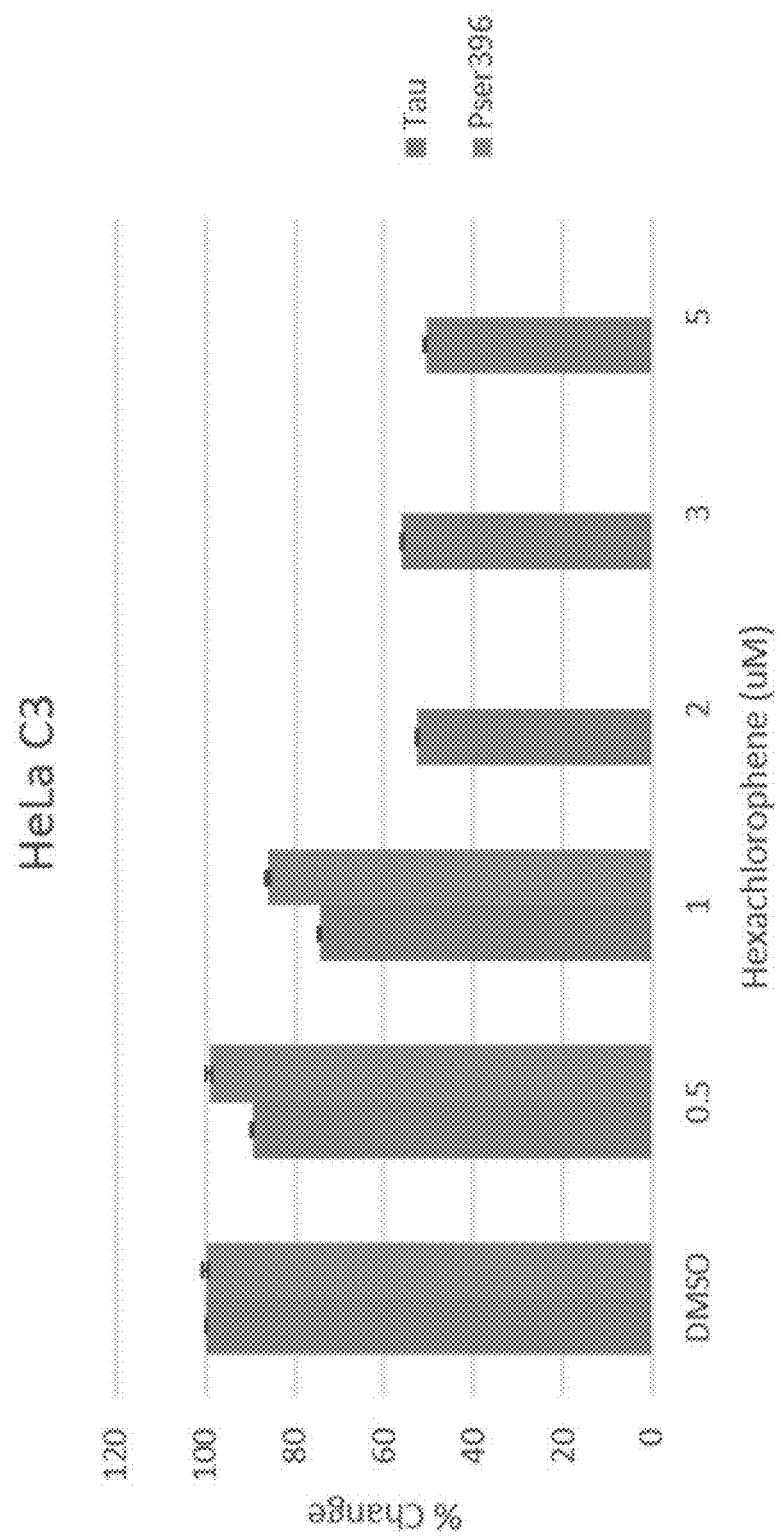
FIG. 2B is a graph showing the change in the level of total tau (left column for each concentration of hexachlorophene) or phosphorylated tau (right column for each concentration of hexachlorophene) after 24 hours of treatment with various amounts of hexachlorophene.

As shown in FIG. 2A and FIG. 2B, hexachlorophene decreased total and phosphorylated tau levels in HeLa C3 cells with over-expressed tau. 2 µM hexachlorophene partially cleared total tau and completely cleared the phosphorylated tau (Pser396).

Figure 3A:
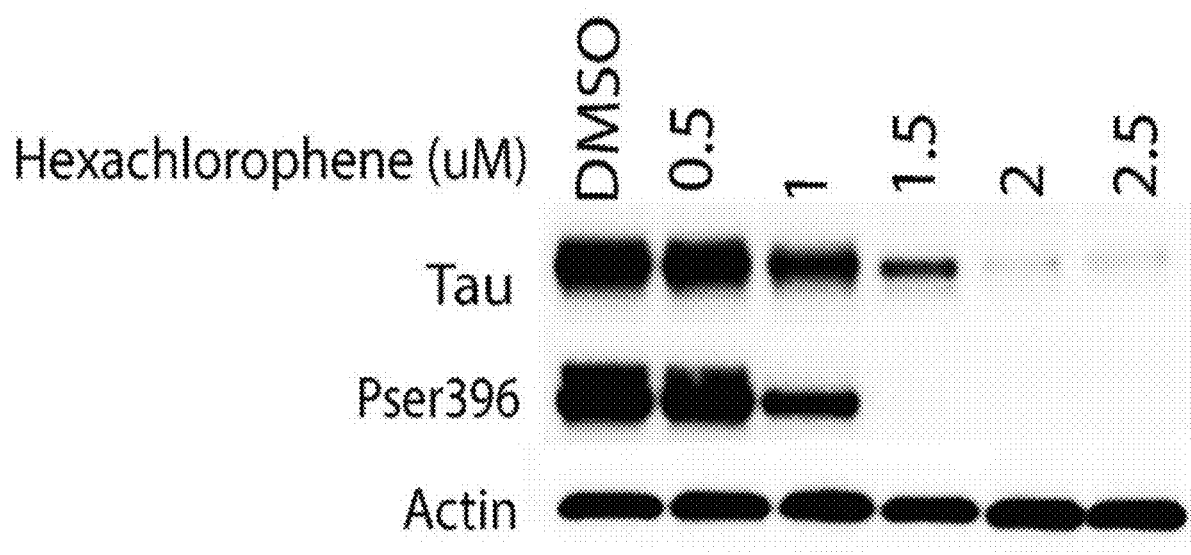
FIG. 3A is a Western blot of cell lysates from iHEK280 cells (inducible tau model) probed with antibodies for total tau, phosphorylated tau, and actin (as a control), after treatment with various amounts of hexachlorophene.
Figure 3B:
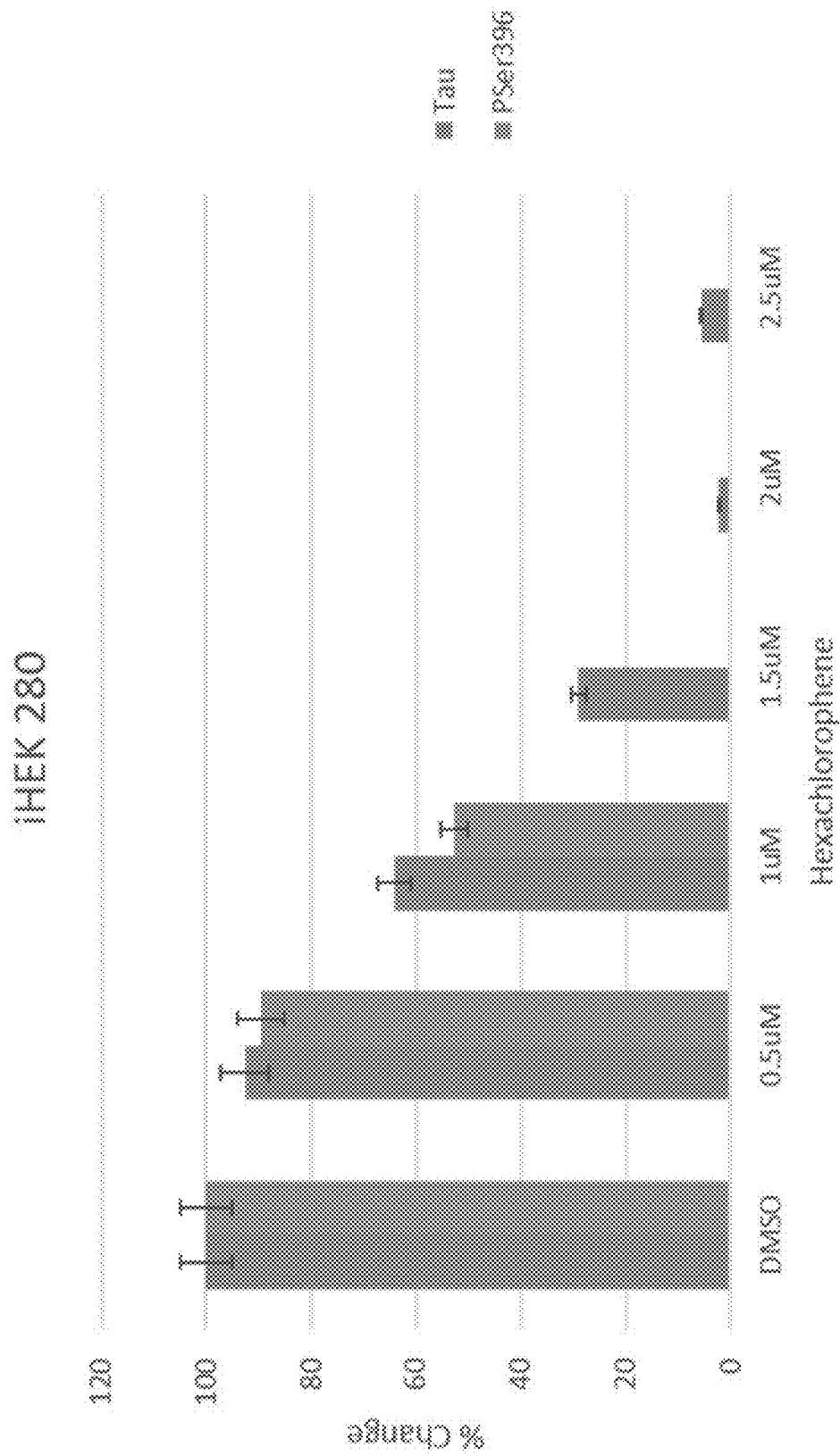
FIG. 3B is a graph showing the change in the level of total tau (left column for each concentration of hexachlorophene) or phosphorylated tau (right column for each concentration of hexachlorophene) after 24 hours of treatment with various concentrations of hexachlorophene.

As shown in FIG. 3A and FIG. 3B, hexachlorophene decreased levels of total and phosphorylated tau in the iHEK280 cell inducible tau model. 1.5 µM hexachlorophene partially cleared the total tau and completely cleared the phosphorylated tau (Pser396). 2 µM hexachlorophene cleared both total tau protein and phosphorylated tau (Pser396) levels.

Hexachlorophene significantly reduced both total and phosphorylated forms of endogenous tau in M17 neuroblastoma cells, inducible tau in HEK280 cells, and over-expressed tau in HeLa C3 cells. In all three cell lines, treatment with hexachlorophene decreased levels of phosphorylated serine 396 tau in the soluble fraction as well.

Example 2

The Effect of Hexachlorophene on Tau Aggregation Using Thioflavin-S Staining

We examined the effect of hexachlorophene on tau aggregation using thioflavin-S staining. Thioflavin S is a mixture of compounds that results from the methylation of dehydrothiotoluidine with sulfonic acid, and it is used to stain tau aggregates. Upon binding tau aggregates, thioflavin S gives a distinct increase in fluorescence emission. Thioflavin-S staining was performed by incubating HEK280 cells with 0.1% thioflavin-S for 5 min, with or without 1 µM hexachlorophene. Cells were also labelled with a primary rabbit polyclonal Tau Antibody diluted with 5% goat serum and a secondary anti-rabbit antibody labeled with red. Cells containing distinct thioflavin-S signals indicating the presence of aggregated protein were scored in many independent fields containing a total of 500 cells.

Figure 4:
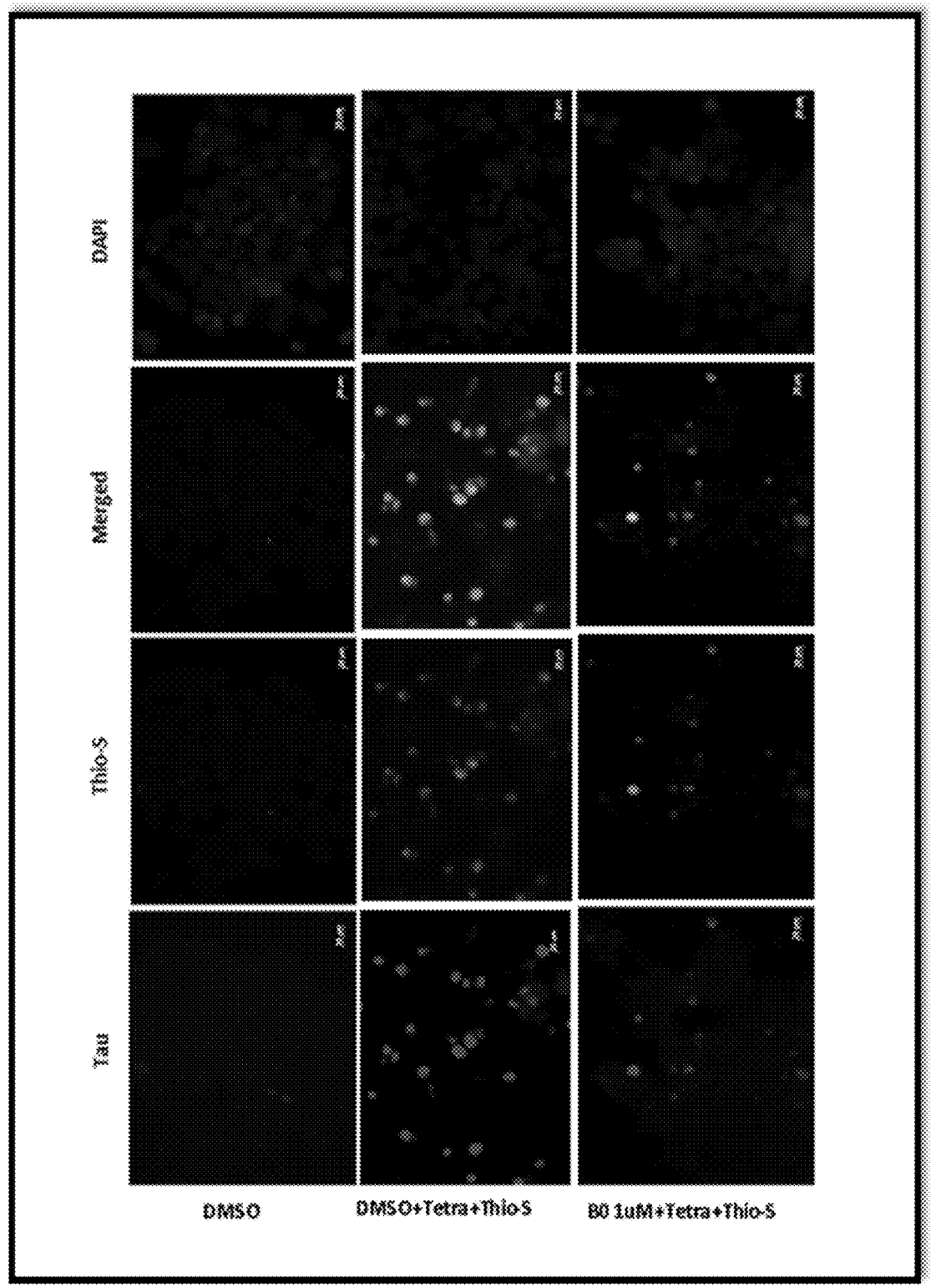
FIG. 4 are images of iHEK280 cells (inducible tau model) stained with thioflavin-S (green) as well as an antibody to tau protein (red). The images show that hexachlorophene targets tau aggregates in iHEK280 cells (an inducible tau model) after 24 hours of treatment.
Figure 5:
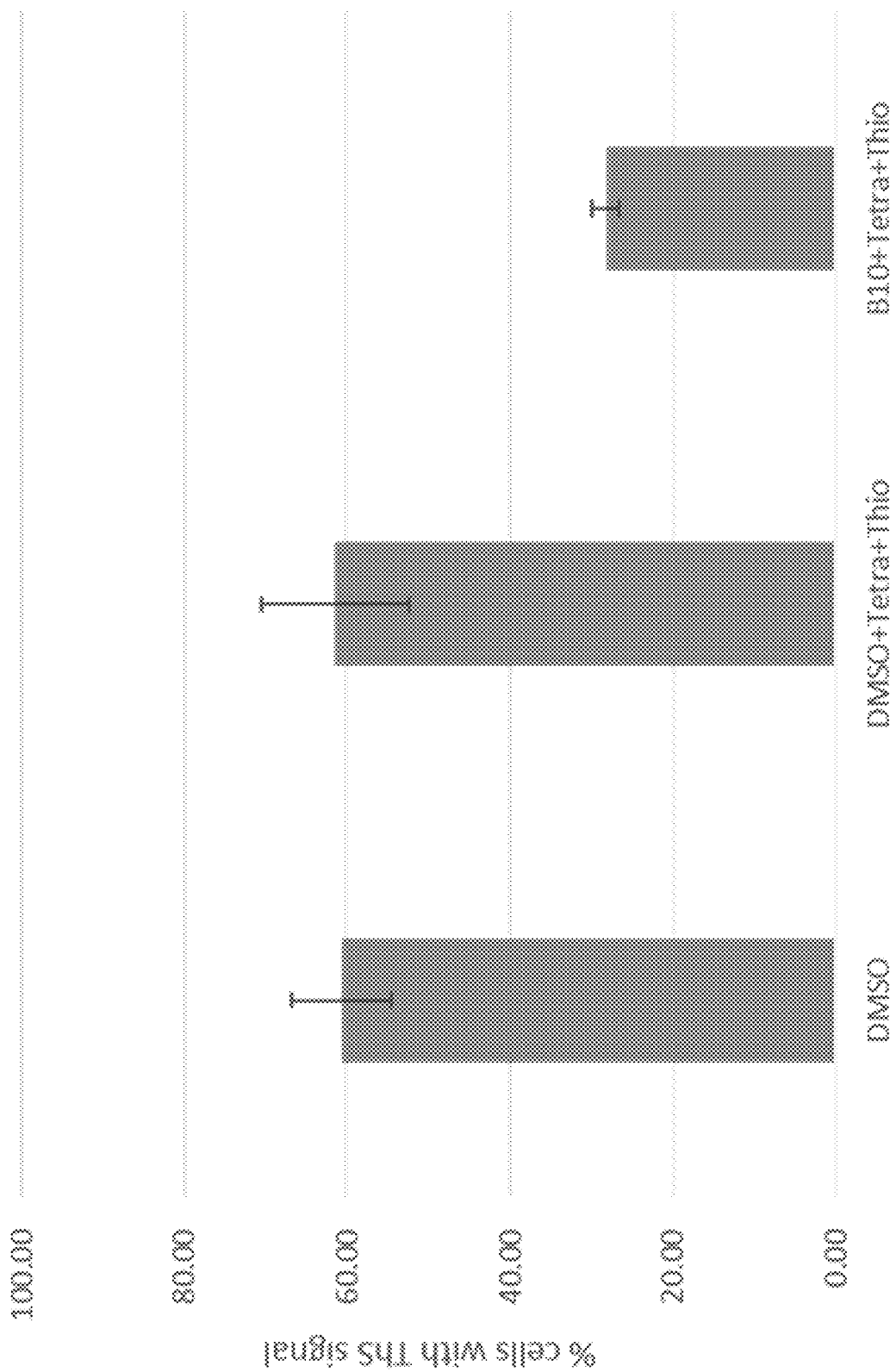
FIG. 5 is a graph showing the percent of iHEK280 cells having a thioflavin-S signal.

As shown in FIG. 4 and FIG. 5, hexachlorophene reduced tau aggregates in HEK280 cells. There was a significant reduction of tau aggregation at a concentration of 1 µM hexachlorophene.

Figure 6A:
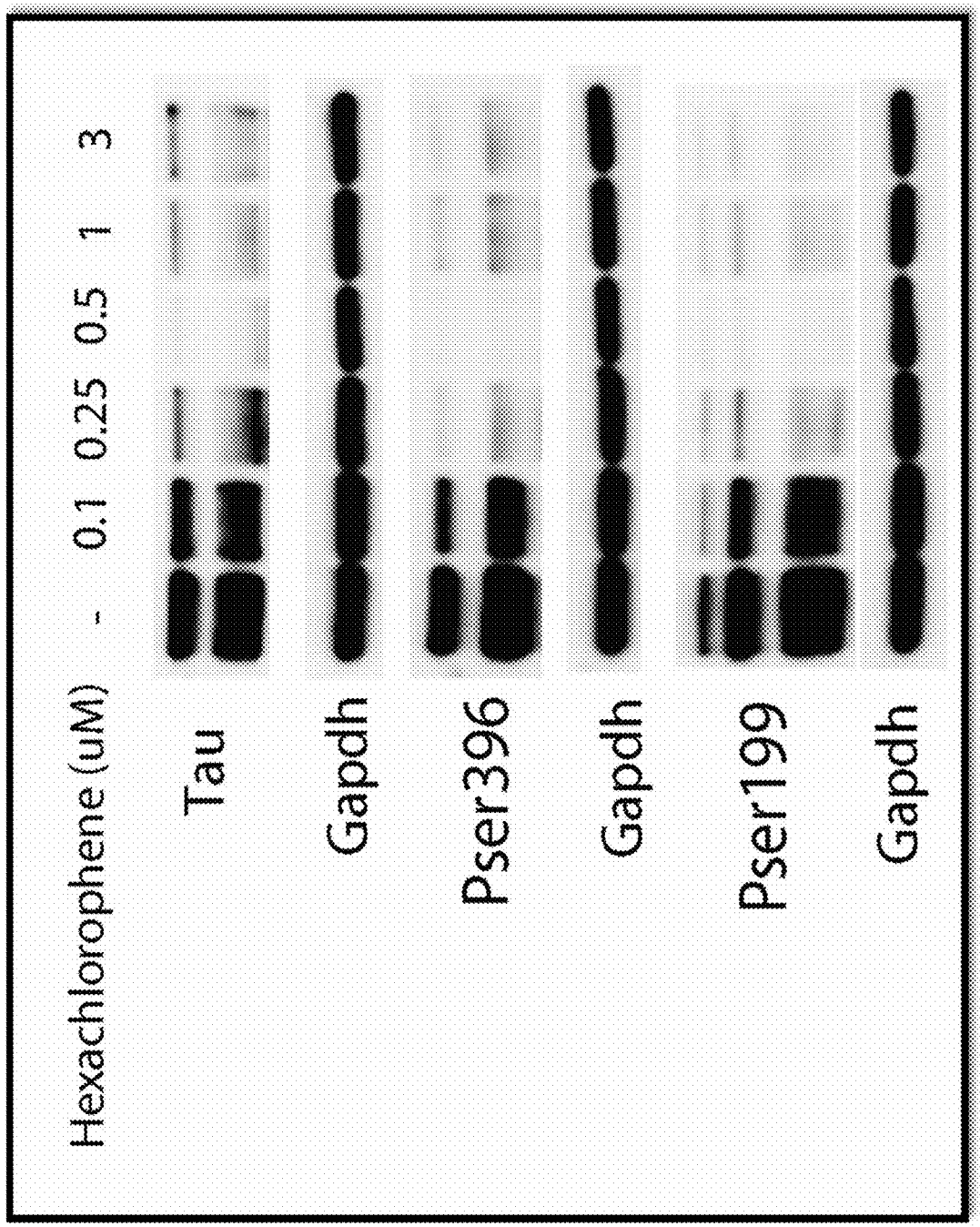
FIG. 6A is a Western blot of cell lysates from neuro-2a mouse neuroblastoma cells overexpressing tau, probed with antibodies for total tau, phosphorylated tau (Pser396 & Pser199), and GAPDH (as a control), after treatment with nanomolar concentrations of hexachlorophene.
Figure 6B:
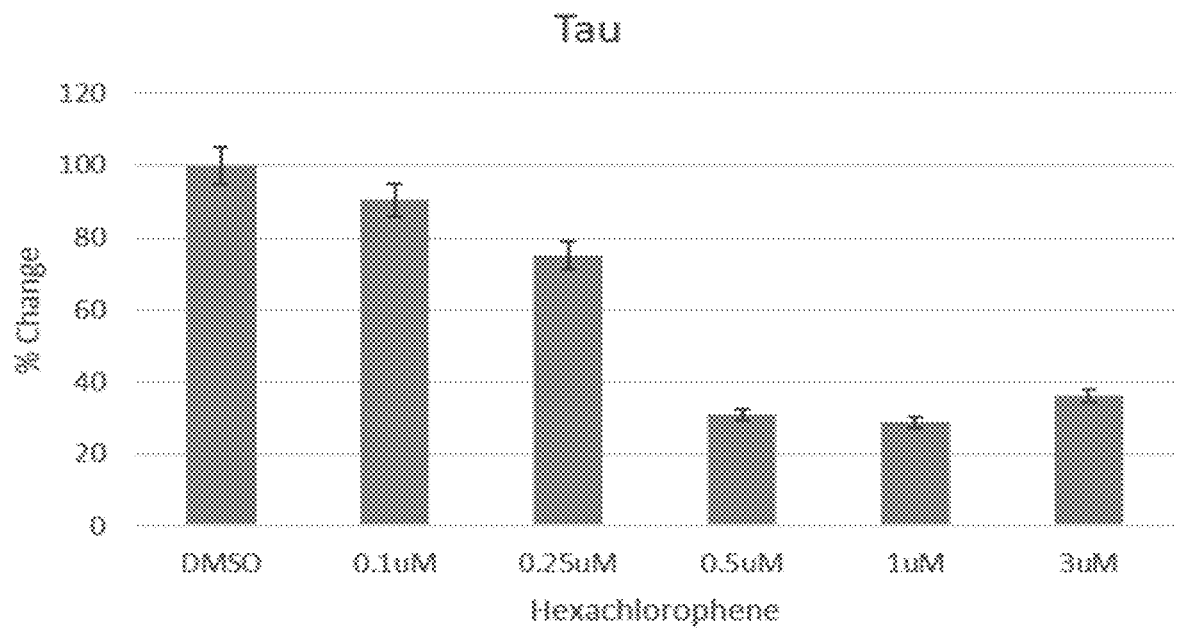
FIG. 6B is a graph showing the decrease in the level of total tau after 24 hours of treatment with nanomolar concentrations of hexachlorophene.
Figure 6C:
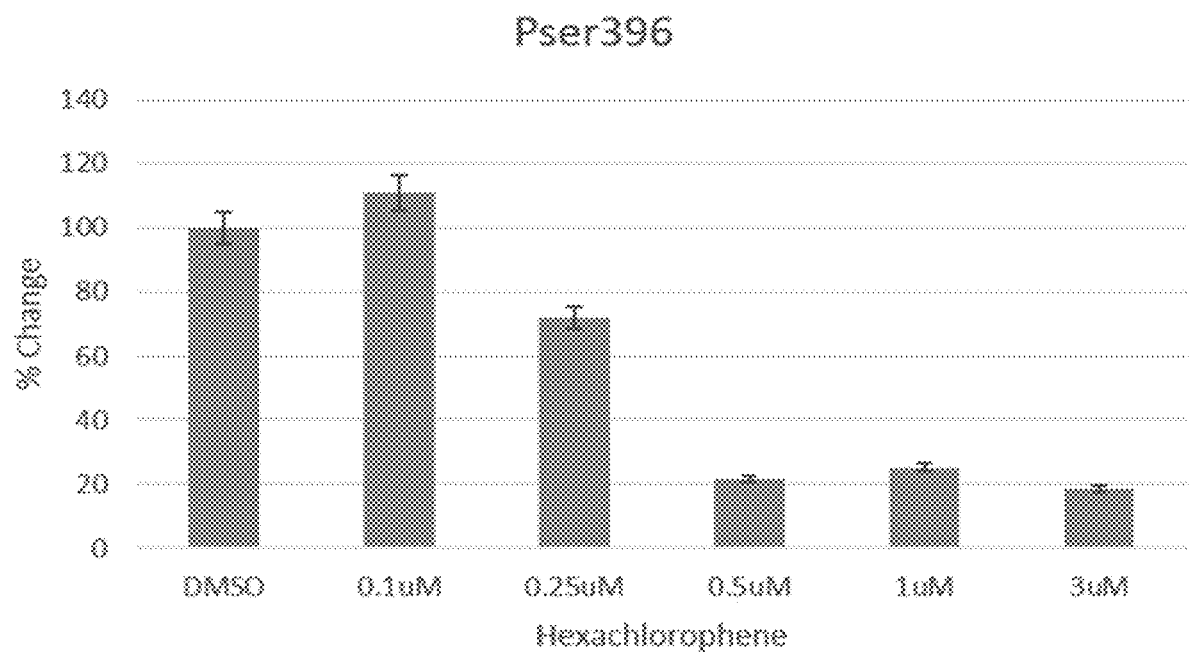
FIG. 6C is a graph showing the decrease in the level of phosphorylated tau (Pser396) after 24 hours of treatment with nanomolar concentrations of hexachlorophene.
Figure 6D:
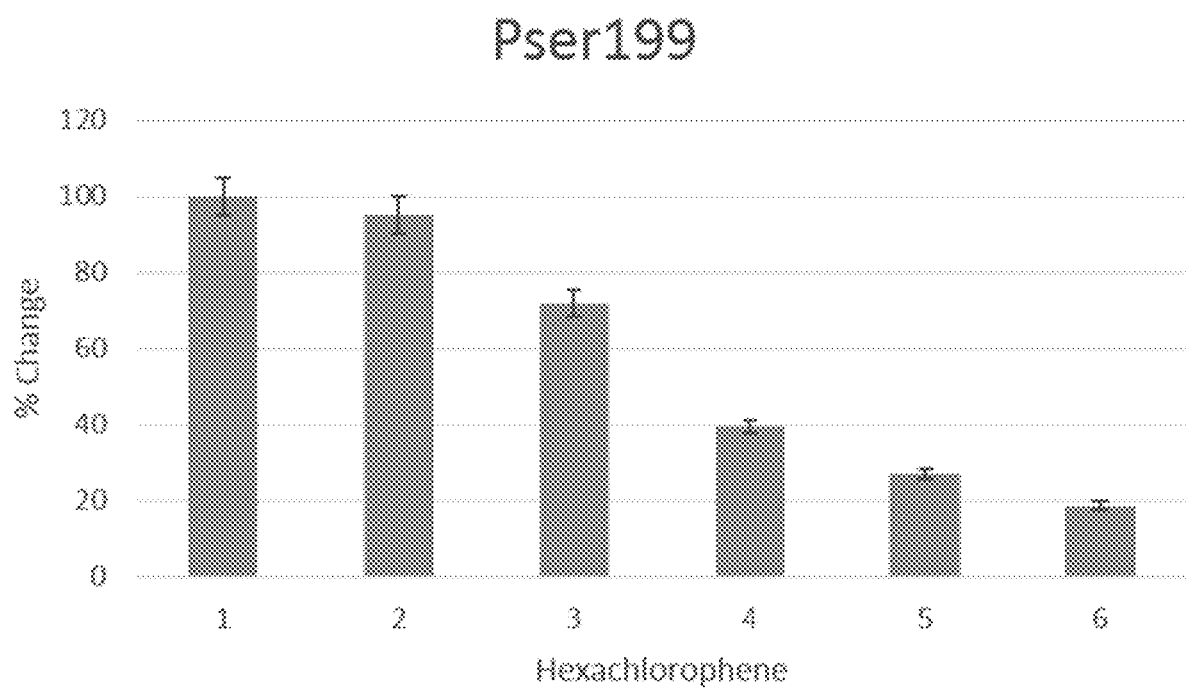
FIG. 6D is a graph showing the decrease in the level of phosphorylated tau (Pser199) after 24 hours of treatment with nanomolar concentrations of hexachlorophene.
Figure 7A:
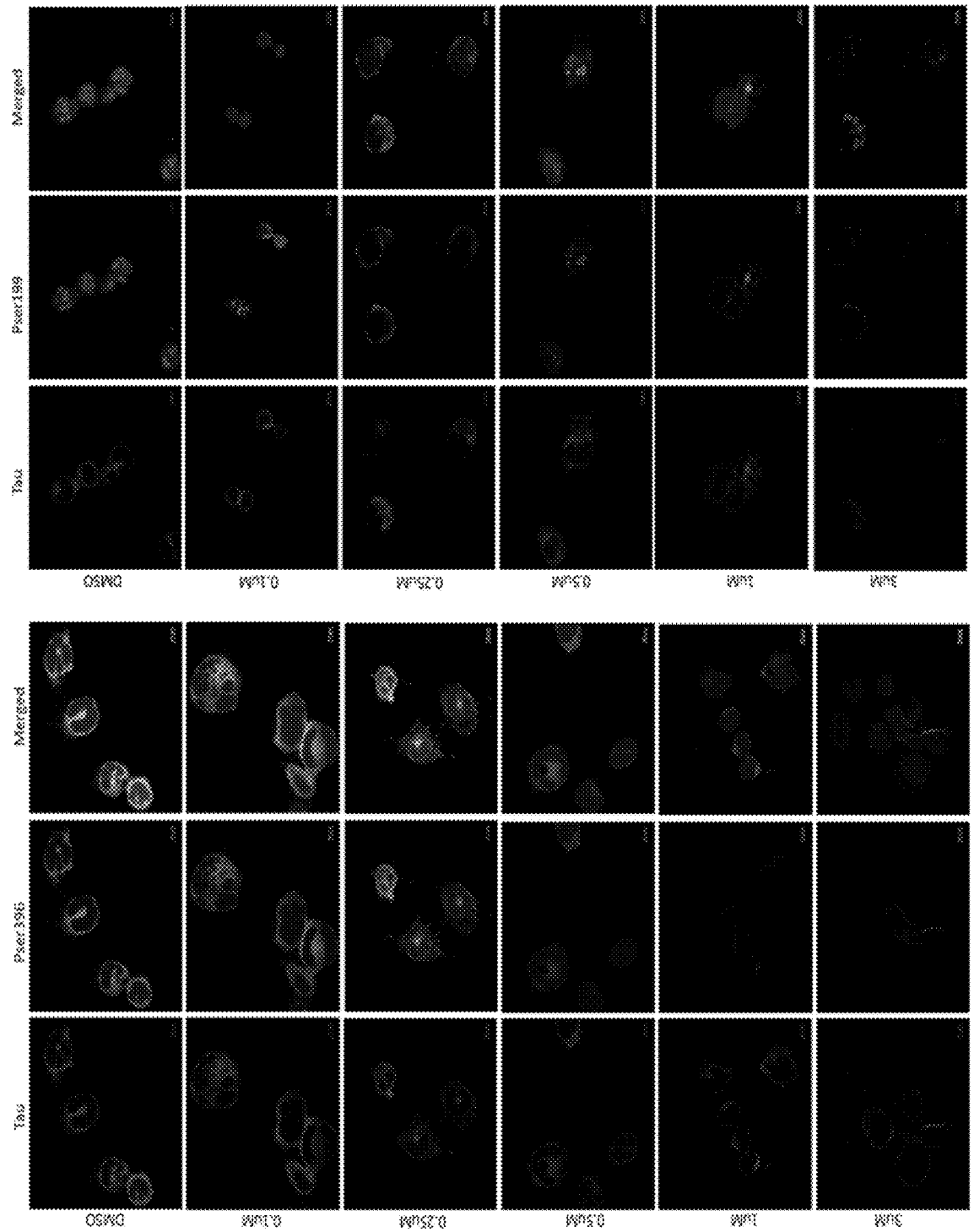
FIG. 7A is an immunofluorescence staining and confocal microscopy analysis of neuro-2a mouse neuroblastoma cells overexpressing tau, showing that hexachlorophene reduces levels of total tau (red) and phosphorylated tau (Pser396-green and Pser199-green) after 24 hours of treatment with nanomolar concentrations of hexachlorophene.
Figure 7B:
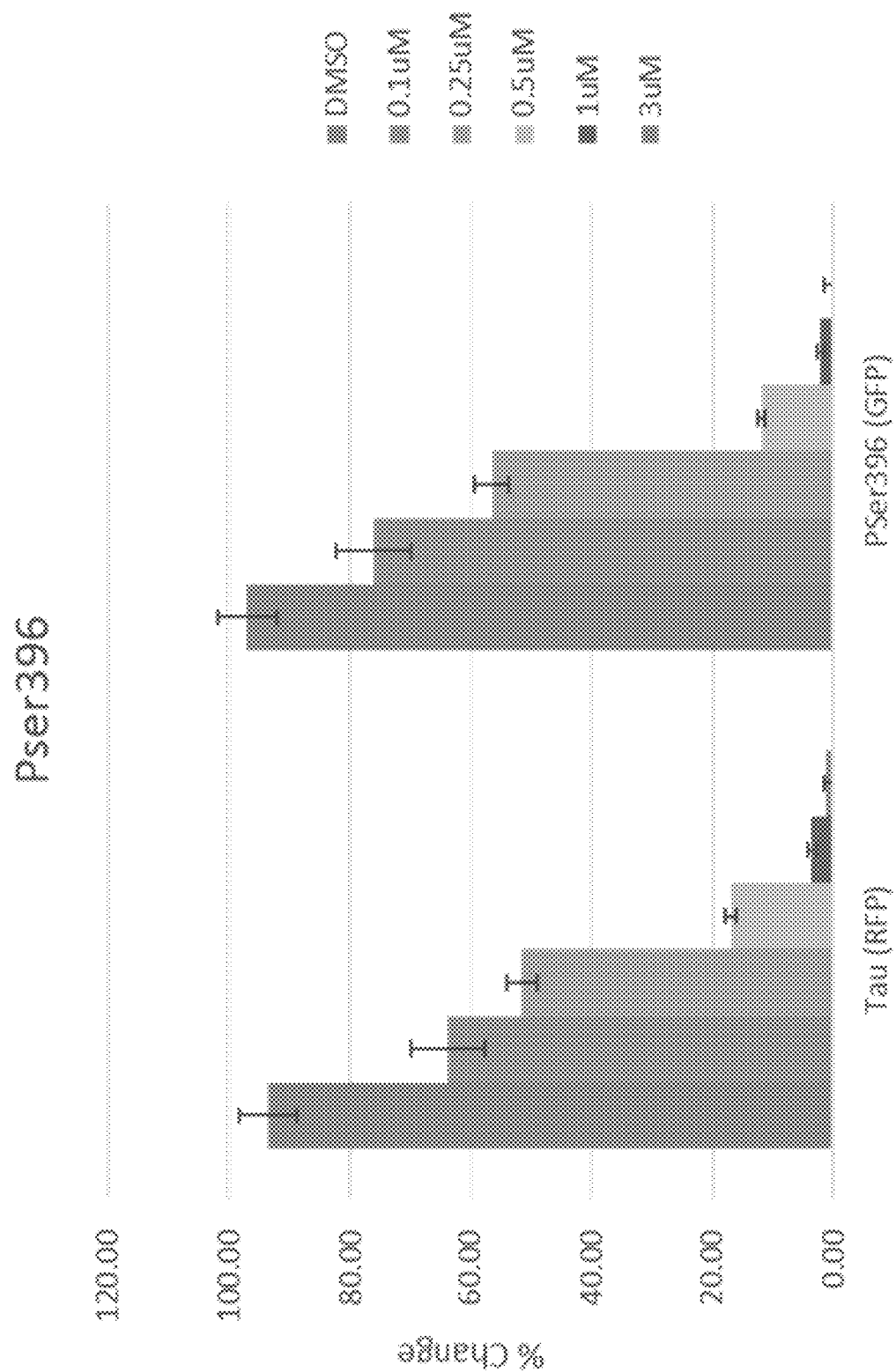
FIG. 7B and FIG. 7C are graphs showing the change in the level of total tau or phosphorylated tau (FIG. 7B for Pser396, and FIG. 7C for Pser199/202) after 24 hours of treatment with nanomolar concentrations of hexachlorophene (from left to right for each set, it is DMSO, 0.1 µM, 0.25 µM, 0.5 µM, 1 µM, and 3 µM hexachlorophene).
Figure 7C:
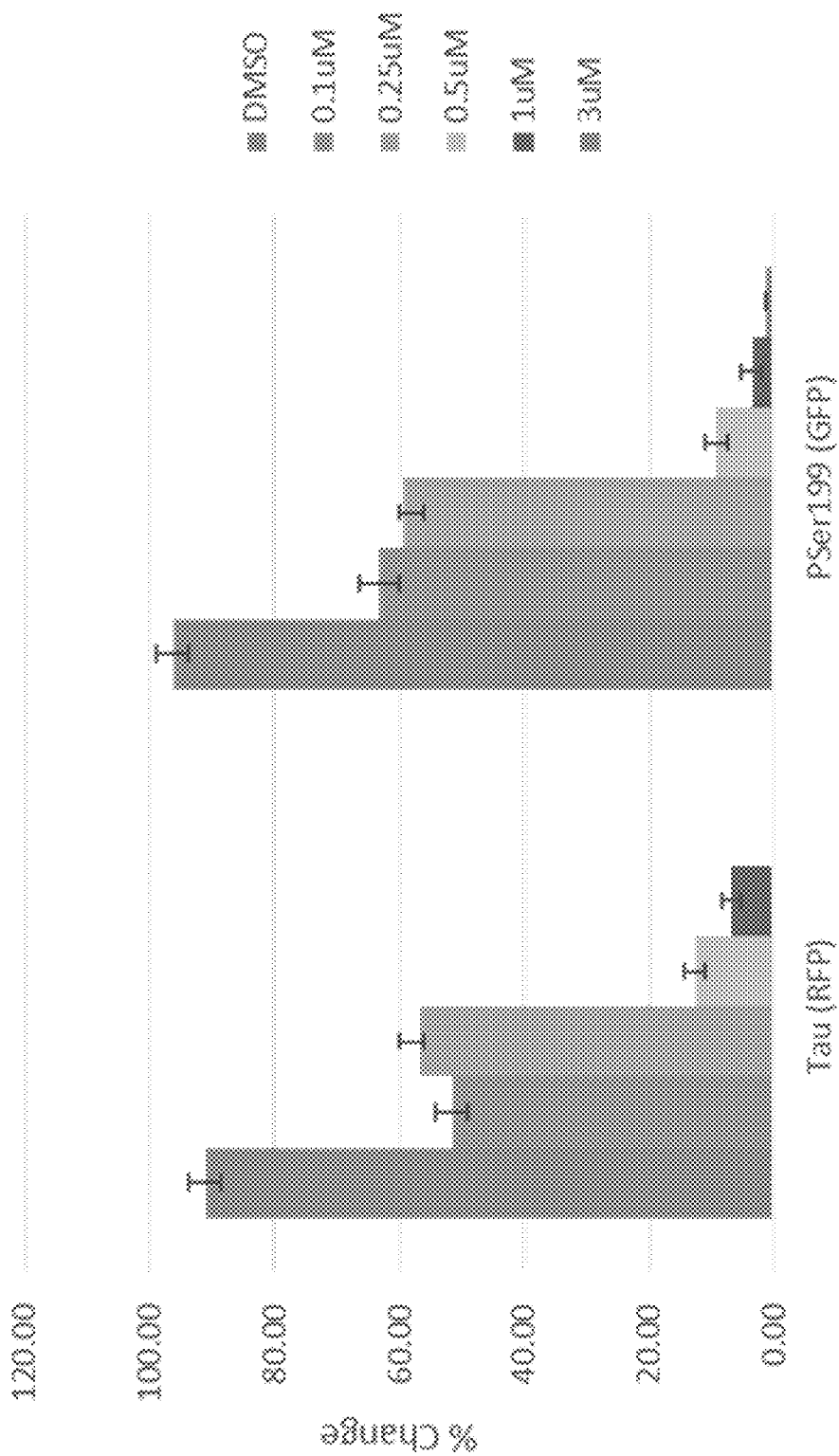

Neuro-2a (N2a) mouse neuroblastoma cells overexpressing human tau-GFP were examined for the effect of hexachlorophene on tau protein using Western blot analysis. As shown in FIG. 6A, hexachlorophene reduced total tau protein and phosphorylated tau, with graphical analysis shown in FIG. 6B, FIG. 6C, and FIG. 6D. Immunofluorescence and confocal microscopy were also used to analyze the effect of hexachlorophene on the cells. As shown in FIG. 7A, hexachlorophene reduced total tau protein and phosphorylated tau, with graphical analysis shown in FIG. 7B and FIG. 7C.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method of treating a tauopathy in a subject, the method comprising administering to the subject a therapeutic amount of hexachlorophene, or a pharmaceutically acceptable salt thereof.

Clause 2. A method of reducing or disrupting tau aggregation in a subject, the method comprising administering to the subject a therapeutic amount of hexachlorophene, or a pharmaceutically acceptable salt thereof.

Clause 3. A method of reducing tau protein in a subject, the method comprising administering to the subject a therapeutic amount of hexachlorophene, or a pharmaceutically acceptable salt thereof.

Clause 4. The method of any one of the preceding clauses, wherein the level of phosphorylated tau protein is reduced.

Clause 5. The method of any one of the preceding clauses, wherein the level of total tau protein is reduced.

Clause 6. The method of clause 4 or 5, wherein the level is reduced a least 10%.

Clause 7. The method of clause 6, wherein the level is reduced at least 50%.

Clause 8. The method of clause 7, wherein the level is reduced at least 80%.

Clause 9. The method of any one of the preceding clauses, wherein tau aggregation is reduced.

Clause 10. The method of clause 9, wherein tau aggregation is reduced a least 10%.

Clause 11. The method of clause 10, wherein tau aggregation is reduced at least 50%.

Clause 12. The method of clause 11, wherein tau aggregation is reduced at least 80%.

Clause 13. The method of any one of the preceding clauses, wherein the tauopathy is selected from neurodegenerative disease, Alzheimer's disease (AD), Parkinson's disease, Huntington's disease, neuronal loss, cognitive defect, primary age-related tauopathy (PART)/Neurofibrillary tangle-predominant senile dementia, chronic traumatic encephalopathy including dementia pugilistica, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

Clause 14. The method of clause 13, wherein the tauopathy comprises Alzheimer's disease (AD).

Clause 15. The method of any one of the preceding clauses, wherein the hexachlorophene or salt is present in a therapeutically effective amount in a pharmaceutical composition.

Clause 16. The method of any one of the preceding clauses, wherein the hexachlorophene or salt is administered to the subject intravenously, intraarterially, or intraperitoneally.

Clause 17. The method of clause 16, wherein the hexachlorophene or salt is delivered to the brain of the subject.

Clause 18. The method of any one of the preceding clauses, wherein the hexachlorophene or salt is administered by gavage.

Clause 19. A pharmaceutical composition comprising hexachlorophene, or a pharmaceutically acceptable salt thereof, for the treatment of a tauopathy in a subject.

Clause 20. The pharmaceutical composition of clause 19, wherein the tauopathy comprises Alzheimer's disease (AD).

The invention claimed is:

1. A method of treating a tauopathy in a subject, the method comprising administering to the subject a therapeutic amount of hexachlorophene, or a pharmaceutically acceptable salt thereof, wherein the level of phosphorylated tau protein is reduced at least 20%, the level of total tau protein is reduced at least 20%, the level of tau aggregation is reduced at least 20%, or a combination thereof.

2. The method of claim 1, wherein the level of phosphorylated tau protein is reduced at least 30%.

3. The method of claim 1, wherein the level of phosphorylated tau protein is reduced at least 40% to 80%.

4. The method of claim 1, wherein the level of total tau protein is reduced at least 30%.

5. The method of claim 1, wherein the level of total tau protein is reduced at least 40% to 80%.

6. The method claim 1, wherein the level of tau aggregation is reduced at least 30%.

7. The method of claim 1, wherein the level of tau aggregation is reduced at least 40% to 80%.

8. The method of claim 1, wherein the tauopathy is selected from neurodegenerative disease, Alzheimer's disease (AD), Parkinson's disease, Huntington's disease, neuronal loss, cognitive defect, primary age-related tauopathy (PART)/Neurofibrillary tangle-predominant senile dementia, chronic traumatic encephalopathy including dementia pugilistica, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

9. The method of claim 8, wherein the tauopathy comprises Alzheimer's disease (AD).

10. The method of claim 1, wherein the hexachlorophene or a pharmaceutically acceptable salt thereof is present in a therapeutically effective amount in a pharmaceutical composition.

11. The method of claim 1, wherein the hexachlorophene or a pharmaceutically acceptable salt thereof is administered to the subject intravenously, intraarterially, or intraperitoneally.

12. The method of claim 11, wherein the hexachlorophene or a pharmaceutically acceptable salt thereof is delivered to the brain of the subject.

13. A method of reducing or disrupting tau aggregation in a subject, the method comprising administering to the subject a therapeutic amount of hexachlorophene, or a pharmaceutically acceptable salt thereof, wherein the level of tau aggregation is reduced at least 20%.

14. The method of claim 13, wherein tau aggregation is reduced at least 30%.

15. The method of claim 13, wherein tau aggregation is reduced at least 40% to 80%.

16. The method of claim 13, wherein the subject suffers from a tauopathy selected from neurodegenerative disease, Alzheimer's disease (AD), Parkinson's disease, Huntington's disease, neuronal loss, cognitive defect, primary age-related tauopathy (PART)/Neurofibrillary tangle-predominant senile dementia, chronic traumatic encephalopathy including dementia pugilistica, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

17. A method of reducing tau protein in a subject, the method comprising administering to the subject a therapeutic amount of hexachlorophene, or a pharmaceutically acceptable salt thereof, wherein the level of phosphorylated tau protein is reduced at least 20%, the level of total tau protein is reduced at least 20%, or a combination thereof.

18. The method of claim 17, wherein the level of phosphorylated tau protein is reduced at least 30%.

19. The method of claim 17, wherein the subject suffers from a tauopathy selected from neurodegenerative disease, Alzheimer's disease (AD), Parkinson's disease, Huntington's disease, neuronal loss, cognitive defect, primary age-related tauopathy (PART)/Neurofibrillary tangle-predominant senile dementia, chronic traumatic encephalopathy including dementia pugilistica, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

20. The method of claim 17, wherein the level of phosphorylated tau protein is reduced at least 40% to 80%.

21. The method of claim 17, wherein the level of total tau protein is reduced at least 30%.

22. The method of claim 17, wherein the level of total tau protein is reduced at least 40% to 80%.

\* \* \* \* \*